(12) United States Patent
Djam et al.

(10) Patent No.: US 10,324,907 B2
(45) Date of Patent: Jun. 18, 2019

(54) GENOMIC APPLICATION DATA STORAGE

(71) Applicant: EMC IP Holding Company LLC, Hopkinton, MA (US)

(72) Inventors: Hamid R. Djam, Rancho Santa Margarita, CA (US); Craig Stewart, Edinburgh (GB); Michael Hancock, Boston, MA (US); Qiyan Chen, Shanghai (CN); Feng Guo, Shanghai (CN); Kay Yan, Shanghai (CN); Dong Xiang, Shanghai (CN)

(73) Assignee: EMC IP Holding Company LLC, Hopkinton, MA (US)

(*) Notice: Subject to any disclaimer, the term of this patent is extended or adjusted under 35 U.S.C. 154(b) by 117 days.

(21) Appl. No.: 14/747,347

(22) Filed: Jun. 23, 2015

(65) Prior Publication Data

US 2015/0286656 A1     Oct. 8, 2015

Related U.S. Application Data

(63) Continuation of application No. 13/804,717, filed on Mar. 14, 2013, now Pat. No. 9,092,451.

(51) Int. Cl.
| | |
|---|---|
| *G06F 16/185* | (2019.01) |
| *G06F 9/50* | (2006.01) |
| *G06F 16/22* | (2019.01) |
| *H04L 12/911* | (2013.01) |
| *G16B 20/00* | (2019.01) |
| *G16B 50/00* | (2019.01) |

(52) U.S. Cl.
CPC .............. *G06F 16/185* (2019.01); *G06F 9/50* (2013.01); *G06F 9/5072* (2013.01); *G06F 16/22* (2019.01); *H04L 47/782* (2013.01); *G16B 20/00* (2019.02); *G16B 50/00* (2019.02)

(58) Field of Classification Search
CPC .................................................. G06F 17/30221
USPC ........................................................ 707/823
See application file for complete search history.

(56) References Cited

U.S. PATENT DOCUMENTS

| | | | | |
|---|---|---|---|---|
| 7,000,141 B1* | 2/2006 | Karlsson | ............... | G06F 9/5011 709/201 |
| 8,291,148 B1* | 10/2012 | Shah | ................... | H04L 67/1097 370/395.21 |
| 8,381,191 B2* | 2/2013 | Mondal | ................... | G06F 9/541 713/177 |
| 2008/0201459 A1* | 8/2008 | Vul | ...................... | H04L 12/2602 709/223 |

(Continued)

*Primary Examiner* — Jensen Hu
(74) *Attorney, Agent, or Firm* — Van Pelt, Yi & James LLP

(57) ABSTRACT

It is decided whether to increase a total amount of storage in a pool of Hadoop storage and whether to increase a total amount of processing in a pool of Hadoop processing. If it is decided to increase the total amount of storage and not increase the total amount of processing, the total amount of storage is increased without increasing processing. If it is decided to not increase the total amount of storage and increase the total amount of processing, the total amount of processing is increased without increasing storage. In response to receiving a request to perform a process on a set of data, processing is allocated from the pool of processing and storage is allocated from the pool of storage where the allocated processing and storage are used to perform the process on the set of data.

18 Claims, 12 Drawing Sheets

(56) References Cited

U.S. PATENT DOCUMENTS

| | | | | |
|---|---|---|---|---|
| 2011/0161497 A1* | 6/2011 | Childress | ............. | G06F 9/5011 709/226 |
| 2012/0144039 A1* | 6/2012 | Watson | ................ | G06F 9/5011 709/226 |
| 2013/0151707 A1* | 6/2013 | Boutin | ................. | G06F 9/5077 709/226 |
| 2013/0268639 A1* | 10/2013 | Myrah | ...................... | G06F 8/76 709/221 |
| 2014/0108639 A1* | 4/2014 | Nelke | ................ | H04L 41/5051 709/224 |
| 2014/0164621 A1* | 6/2014 | Nakama | .................. | H04L 47/70 709/226 |
| 2014/0172809 A1* | 6/2014 | Gardella | ........... | G06F 17/30575 707/705 |
| 2014/0181816 A1* | 6/2014 | Muller | ................. | G06F 9/5022 718/1 |
| 2014/0245298 A1* | 8/2014 | Zhou | ...................... | G06F 9/455 718/1 |

\* cited by examiner

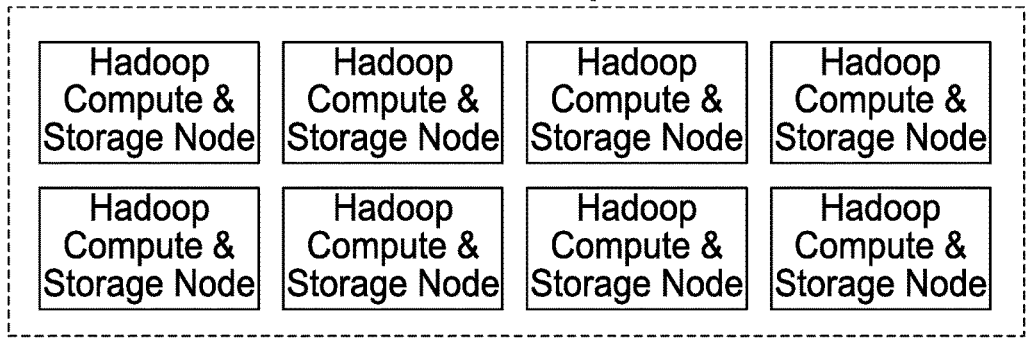
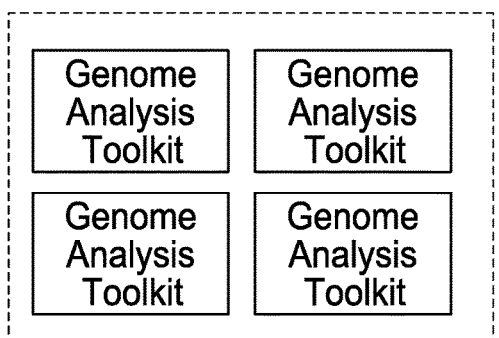
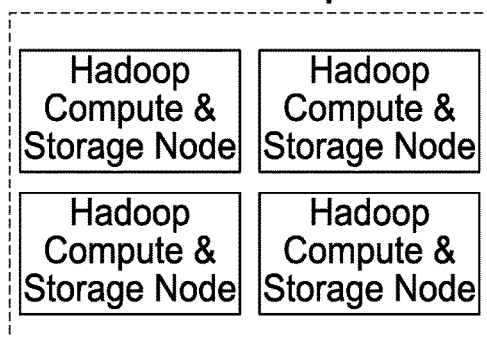
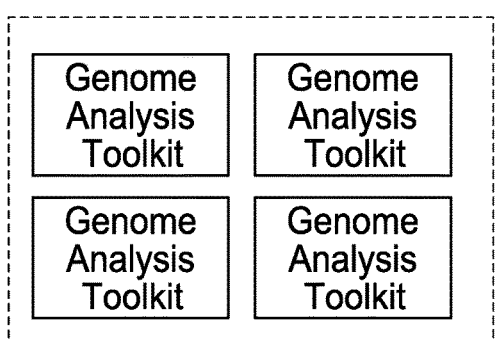
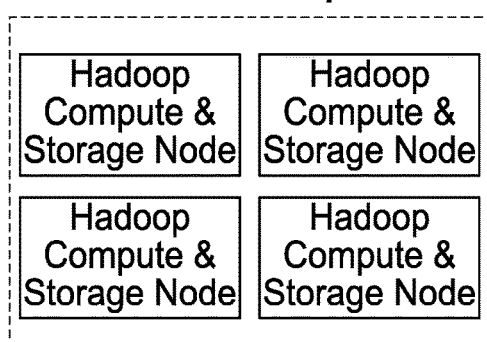
FIG. 1A

Account Setup 200

| | | |
|---|---|---|
| School: | School of Medicine ▽ | 202 |
| Department/Institute: | Genetics ▽ | 204 |
| Lab/Principal Investigator: | Mary Johnson Lab | 206 |
| Username: | Mary.Johnson.Lab | 208 |
| Password: | •••••••• | 210 |
| Budget (Optional): | $10,000 | 212 |
| | ● Annually  ○ Semi-annually  ○ Quarterly | 214 |
| Permission Required? | ● Yes  ○ No | 216 |
| Contact Name: | Mary Johnson | 218 |
| Contact E-mail: | mary.johnson@abc.edu | 220 |

Enter

FIG. 2

Processing Service — 600

| Start a New Process | Previous Results | Account Information | 602 |

Account Activity: — 610

| | Credit | Debit | Remaining Budget |
|---|---|---|---|
| March 1, 2013 Run | | $190 | $9,605 | ← 612
| February 15, 2013 Payment | $205 | | | ← 614
| February 6, 2013 Run | | $205 | $9,795 | ← 616

Account Settings: — 620

| School: | School of Medicine | ← 622 |
| Department/Institute: | Genetics | ← 624 |
| Lab/Principal Investigator: | Mary Johnson Lab | ← 626 |
| Budget (Optional): | $10,000 | ← 628 |

● Annually  ○ Semi-annually  ○ Quarterly ← 630

Permission Required?  ● Yes  ○ No ← 632

| Contact Name: | Mary Johnson | ← 634 |
| Contact E-mail: | mary.johnson@college.edu | ← 636 |

[ Update ]

FIG. 6

GENOMIC APPLICATION DATA STORAGE

This application is a continuation of co-pending U.S. patent application Ser. No. 13/804,717, entitled GENOMIC APPLICATION DATA STORAGE filed Mar. 14, 2013 which is incorporated herein by reference for all purposes.

BACKGROUND OF THE INVENTION

Genome data often comprises very large datasets and so processing of genome data (e.g., by researchers) cannot be done easily and/or in a reasonable amount of time using just any processing system. To manage such large datasets, distributed systems which can handle very large datasets are often used (e.g., Hadoop systems). FIG. 1A is a diagram showing an example of a university (or a company) in which researchers build their own systems for processing genome data and do not share systems with other researchers, even though those other researchers may work for the same university or company. This is an inefficient use of resources, since such systems will be sitting idle most of the time. New systems which can process and/or store very large datasets, such as genome data, would be desirable.

BRIEF DESCRIPTION OF THE DRAWINGS

Various embodiments of the invention are disclosed in the following detailed description and the accompanying drawings.

FIG. 1A is a diagram showing an example of a university (or a company) in which researchers build their own systems for processing genome data and do not share systems with other researchers, even though those other researchers may work for the same university or company.

FIG. 2 is a diagram showing an embodiment of a user interface for setting up an account.

FIG. 6 is a diagram showing an embodiment of a user interface which shows account information.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1B:
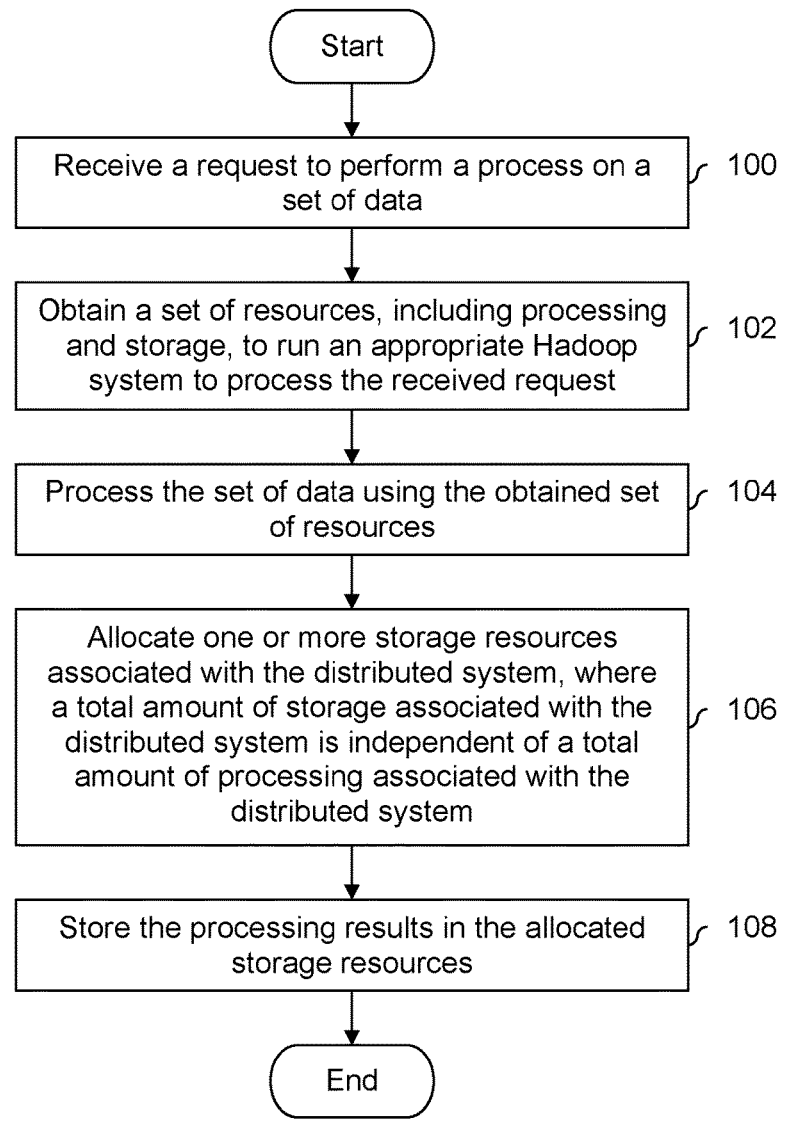
FIG. 1B is a flowchart illustrating an embodiment of a process for providing a processing service.

FIG. 1B is a flowchart illustrating an embodiment of a process for providing a processing service. In one example, a company or university builds a processing system which performs the process of FIG. 1B and makes the system available to its employees. As will be described in further detail below, in some embodiments, requests from different users (e.g., from different primary investigators or labs at a university or different employees at a company) are able to be serviced simultaneously without sharing information with other users unless permitted. In some embodiments, users from different companies or entities are serviced (e.g., the provided processing service is a third-party service and users who are willing to pay for the service are permitted to use the service).

At 100, a request to perform a process on a set of data is received. For example, the set of data may include genome data and a researcher wants to perform one or more processes on the data, such as genome typing or generating statistical information about the genome data (e.g., determining correlations or distributions).

At 102, a set of resources, including processing and storage, is obtained to run an appropriate Hadoop system to process the request received at 100. Processing resources for a new distributed Hadoop system are allocated and the Hadoop software is provisioned via automated build processes (one example Hadoop software distribution is Pivotal HD). In one example, there is a pool of processing and storage resources associated with the newly provisioned Hadoop system created to deal with the request at 100. Some portion or all of the pool of allocated resources will be used to service the request received at 100, in some cases a portion of the pool may be kept in reserve (e.g., so that if a request from another user is received, there are processing resources still available). Automation and orchestration of resource allocation, storage allocation and Hadoop system provisioning are key components of the platform. In one example, automation is provided by the vCloud Automation Center product from VMware (known as vCAC). In the example above, processing resources are virtual and VMware vCloud Director is orchestrated by VCAC to allocate a virtual processing resource at 102. Provisioning of storage resources on the Isilon scale out NAS platform (for example) is carried out by VCAC in parallel with EMC Integrated Storage Management (ISM) making calls to the Isilon API to automate storage provisioning tasks. Provisioning of virtual Hadoop compute nodes is done (at least in this example) through a combination of VMware Serengeti and Pivotal HD; these Hadoop compute nodes will be held as templates on the infrastructure and deployed based on the request made at 100. Customization of the Hadoop nodes to meet the specific demands of the request at 100 may be done through custom scripts; this includes the linking of the Hadoop compute nodes to the Pivotal HD Hadoop File System stored directly on the Isilon scale out NAS array.

As is described above, in some embodiments, a processing resource allocated at 102 is a virtual processing resource. A virtual processing resource may be attractive because an application or toolkit which runs on a virtual processor is decoupled from the specific implementation of the underlying processor below the virtualization. This enables a variety of underlying processors to be employed and if a switch of underlying processors is desired, such a change is transparent to the application or toolkit because of the virtualization.

At 104, the set of data is processed using the obtained set of resources. For example, the exemplary genome data may be processed using the Broad Institute's genome analysis toolkit where the toolkit runs on the processing and storage resources allocated at 102. In some embodiments, processing at 104 requires resources additional resources, such as ports (sometimes referred to as I/Os). In such embodiments, those resources are allocated prior to processing the set of data at 104.

At 106, one or more storage resources associated with the distributed system are allocated, where a total amount of storage associated with the distributed system is independent of a total amount of processing associated with the distributed system. Similar to the example associated with step 102 described above, in some embodiments there is a pool of storage and some portion of the pool is allocated at 106 to service the request. In some embodiments, a storage resource allocated at 106 is virtual (e.g., and VMware vCenter Server and/or VMware vCloud is used to allocate a virtual storage resource at 106).

The processing results are stored in the allocated storage resources at 108. For example, the storage may be network attached storage (NAS), such as EMC Isilon storage. In one example, processing at 104 includes processing genome data using a genome analysis toolkit and generating results in the form of a variant call format (VCF) file. A VCF file may contain unstructured data and in some embodiment the VCF file is transformed into relational data capable of being stored on and/or accessed from a relational database (e.g., the data is transformed to have column and/or row formatting in order to "fit" in a relational database). In one example, a transformation from unstructured data to relational data is performed using Greenplum HD.

In some embodiments, transformed relational data (e.g., transformed using Greenplum HD) is stored at 108 in a massively parallel processing (MPP) database which is designed or optimized to analyze very large datasets (e.g., on the order of terabytes or petabytes). One example of a MPP database is Greenplum Database. Greenplum Database (or other alternatives) may be attractive because such database applications offer a suite of database analysis tools designed for very large datasets. With the data is saved in relational form in Greenplum Database (or some other alternative), subsequent analysis is faster than having to transform the data into relational form each time before analysis, or trying to analyze the data in unstructured form. Another advantage to storing processing results in Greenplum Database (or some other alternative) is that such applications work seamlessly with other applications or tools which have additional or different features. For example, Greenplum Chorus, which enables sharing of data with collaborators or other select users, works seamlessly with Greenplum Database.

In some embodiments, a user associated with a request is charged by the system. For example, a company or university may make a processing system available to its employees or researchers but charges a user depending upon the processing resources allocated at 102 and/or the storage resources allocated at 106. In some embodiments, a university gives each PI or lab a certain amount of credit and after the credit is used up the lab must pay for service. In some embodiments, a processing system is a third-party service available to any user who is willing to pay for the service. In such embodiments, FIG. 1B includes determining a cost (e.g., based on the amount of processing allocated at 102 and/or the amount of storage allocated at 106) and recording the cost. The cost may be saved in the account of the user who submitted the request at 100 so that the proper party is charged for service.

One feature of the process shown in FIG. 1B is that the total amount of storage associated with the distributed system is independent of the total amount of processing associated with the distributed system. For example, processing and storage on the distributed system are decoupled (an example of this is described in further detail below). For such systems, when the total amount of storage (as an example) is increased, it does not necessitate a corresponding increase in the total amount of processing. To a company or university which builds a system which performs the process of FIG. 1B, this is an attractive feature because additional processing resources may not be required. For example, the total amount of processing in a system may be sufficient to service the level of requests coming in from all users, so it is not necessary to increase the total amount of processing. Distributed systems with decoupled storage and processing do not require the purchase and installation of additional processing which would be underutilized.

In contrast, some other systems have coupled storage and processing. For such systems, scaling up the total amount of storage (as an example) would also require a corresponding increase in the total amount of processing. This is undesirable because even before the increase in processing, the total amount of processing may be more than sufficient. For example, in some distributed systems where processing and storage are coupled and storage is the limiting factor, only about 5% of the total amount of processing is utilized, which is a significant underutilization.

Another feature of the process shown in FIG. 1B is that any amount of processing may be allocated at 102 and any amount of storage may be allocated at 106. Using genome data as an example, processing and/or storage requirements may vary greatly depending upon the processes being performed and the data being processed. For example, performing genome typing on one set of genome data may have very different processing and/or storage requirements than a correlation analysis performed on another set of genome data. Being able to allocate an amount of storage independent of the amount of processing is desirable because a request can be serviced without allocating excess processing or storage resources. This is a desirable feature in a multi-user system.

In contrast, some other distributed systems were built by individual users for their personal use and were not intended to be shared with other users. As such, those other systems do not necessarily allocate storage resources and/or allocate processing resources. One difference between such other systems and the process shown in FIG. 1B is that those other systems may not be able support multiple users while keeping data confidential. For example, processing results stored at 108 in allocated storage resources are only available to the user who requested the service whereas processing results in other systems may be visible to any user. This may be undesirable, even if all users work for the same company or university. For example, some large research universities hire junior faculty in the same area of research (i.e., deliberately pitting colleagues at the same university against each other) with the understanding that the researcher who produces the best work will be offered tenure. In such a competitive environment, it is undesirable for one researcher to be able to see another researcher's work.

Another benefit of allocating processing at 102 and storage at 106 is evident in systems where the services provided by FIG. 1B have costs associated with them. For example, a university may make processing services available to its researchers but charges a researcher based on the amount of processing allocated at 102 and/or the amount of storage allocated at 106. Being able to allocate varying amounts of storage resources at 102 and/or processing resources at 106 enables a system (if desired) to allocate resources in a manner that satisfies some cost constraint. For example, a less established researcher with less grant money may want to spend less money on processing services than a more established researcher with more grant money.

The following figures show a variety of user interfaces associated with various steps of FIG. 1B. These figures are merely exemplary and are not intended to be limiting. For example, although certain user interface controls are shown (e.g., pull down menus, radio buttons, etc.), other user interface controls may be used. Also, the exemplary user interfaces are associated with a university which makes a processing system available for use by its researchers and therefore some information about potential users is known a priori (e.g., schools, departments, mailing addresses, and/or names of potential users). Some other scenarios (e.g., where a third-party processing system is made available to any user from any university or company) may require other information to be obtained and/or presented (e.g., a mailing address to send invoices to). Also, although genome data and processing of such data is used in the examples below, this is not intended to be limiting and the systems and techniques described herein may be used with any large dataset. For example, weather or climate models often comprise large datasets.

FIG. 2 is a diagram showing an embodiment of a user interface for setting up an account. In the example shown, a processing system is provided by a research university for use by its researchers. Researchers set up accounts via user interface 200. Once an account is set up, a researcher (or someone in their lab) is able to access the services of the processing system and be billed accordingly.

Using pull down menu 202, the user's school is identified as the school of medicine. In this example, once pull down menu 202 is specified, pull down menu 204 is populated with the departments and/or institutes for the specified school. For example, the school of medicine may have one set of departments/institutes and whereas the school of engineering has another set, and pull down menu 204 is populated accordingly depending upon the school specified in pull down menu 202.

The user's department is identified as the genetics department in pull down menu 204. The lab or principal investigator (PI) with which the user is associated with is specified in fillable field 206 to be the Mary Johnson lab. As used herein, the terms lab and PI are used interchangeably since for the purposes of explanation it is assumed a lab includes only one principal investigator and that it is permissible to share confidential information amongst people in the same lab. In fillable field 208, the username is set to Mary.Johnson.Lab and the password is specified via fillable field 210.

User interface 200 offers the user the option of specifying a budget in fillable field 210 and the period of time (e.g., annually, semi-annually, or quarterly) over which the specified budget applies. In some embodiments, a specified budget is a soft budget, which is tracked for the convenience of the user but is not necessarily used to disable services if the budget is exceeded. In some embodiments, budget field 212 is pre-populated depending upon the PI. For example, a school or department may allocate or credit a certain amount of money to each PI, and budget field 212 indicates the amount of money credited to the PI specified (e.g., via user interface controls 202, 204, and/or 206). In some embodiments, a budget is a hard limit, and access to the processing system is denied if the budget is zero or negative, or if the cost of a processing run would exceed the available budget. In various embodiments, services must be pre-paid (e.g., sending in money for credit on the system before the services are used) or services may be paid for after the fact.

User interface 200 also permits a user to control whether permission is first obtained before a processing run is performed. If permission is required, the contact person (where the contact name is specified in fillable field 218 and the contact email address is specified in fillable field 220) is contacted for approval before a processing run is performed.

Figure 3:
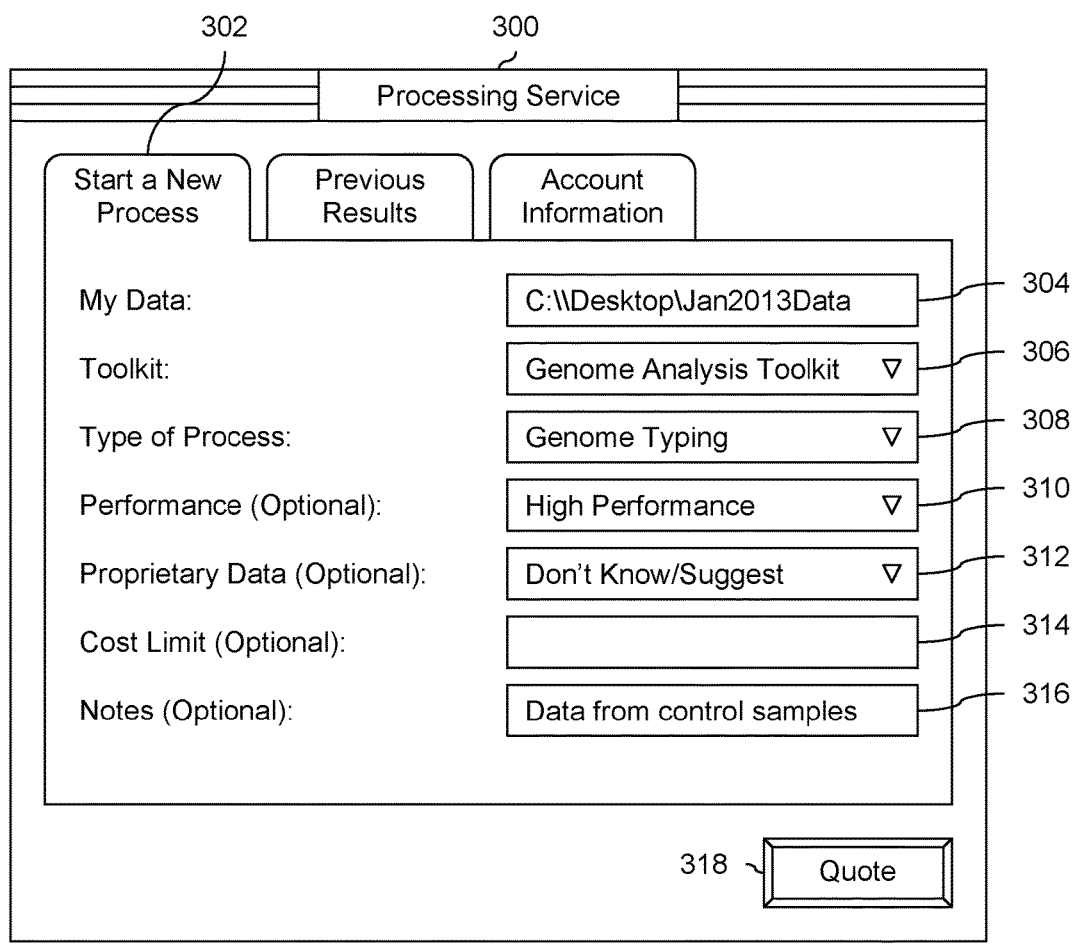
FIG. 3 is a diagram showing an embodiment of a user interface for specifying a new processing run.

FIG. 3 is a diagram showing an embodiment of a user interface for specifying a new processing run. In the example shown, a user wants to perform a genome related process and selects tab 302 (i.e., start a new process) in user interface 300 in order to set up the desired processing run. The user's data (e.g., collected by the researcher or user) is specified in field 304 (e.g., after going through a file system hierarchy) and a desired toolkit (i.e., genome analysis toolkit) is specified in pull down menu 306. The type of process (in this example, genome typing) is specified in pull down menu 308.

Pull down menu 310 is an option in which the user can specify a desired level of performance. The user in this example has selected high performance, but other performance options (e.g., moderate performance, budget/low performance, etc.) may be selected. Costs scale with performance in this example, so better performance will cost more money.

In this example, proprietary data may be specified in optional pull down menu 312. In this genomics related example, proprietary data may comprise genome sequences owned by a third party to whom royalties or payments are made if the proprietary data is used in the processing. In this particular example, pull down menu 312 is set to don't know/suggest. In some embodiments, when this option is set, the data specified in field 304, the toolkit specified in pull down menu 306 and/or the type of process specified in pull down menu 308 is used to determine relevant proprietary data (if any). For example, the data specified in field 304 may relate to certain locations in a genome or certain markers and appropriate proprietary data (e.g., which covers those locations or markers) is selected by pre-processing the data specified in 304.

Optional cost limit fillable field 314 is used to specify (if desired) a cap on the processing run being specified. If specified, the processing run which is quoted will try to stay within the specified cost limit.

Optional notes field 316 is used to record a user's notes. In this particular example, the user's notes indicate that the data (e.g., specified in field 304) comprises control samples. A note may be saved with and/or associated with its corresponding processing run, for example so that even if more than one person is working with the data, a person who did not initiate the processing run knows what the processing run relates to and/or has sufficient context to interpret or make sense of the processing results.

Once the user has set the fields in tab 302 to the desired values, the user presses quote button 318 and receives a proposed processing run. The following figure shows an example of a returned proposed processing run.

Figure 4:
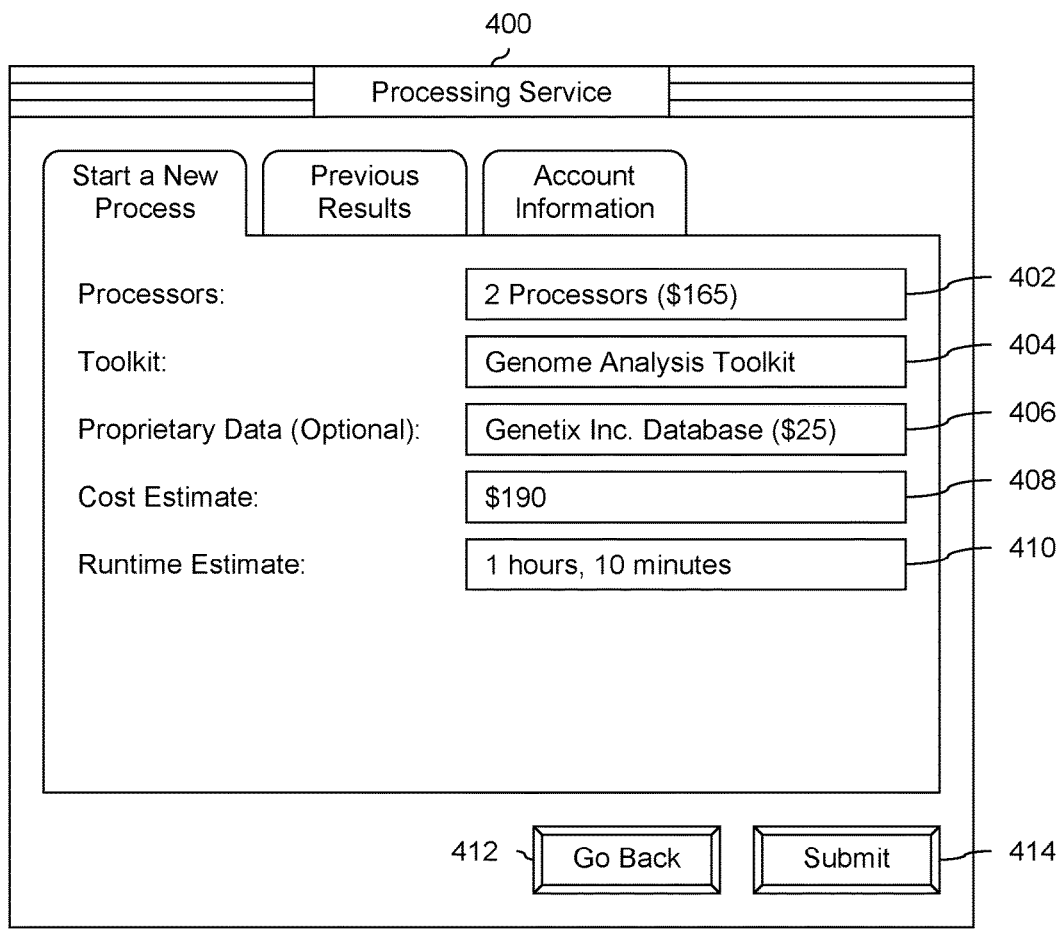
FIG. 4 is a diagram showing an embodiment of a user interface which presents a proposed processing run.

FIG. 4 is a diagram showing an embodiment of a user interface which presents a proposed processing run. Based on the information specified in FIG. 3, user interface 400 proposes the shown processing run. In field 402, the proposed processing run includes two processors at a cost of $165. Although this particular example only varies the number of proposed processors, in some embodiments, different processing resources have different performance capabilities and field 402 in some embodiments includes both quantity and quality of processors (e.g., 1 high end processor and 1 mid-range processor).

The toolkit for the proposed run is shown in field 404 and the proprietary data is shown in field 406. In this particular example, proprietary data field 312 in FIG. 3 was set to don't know/suggest and the processing system (e.g., based on its analysis) is proposing to use the Genetix Inc. database at a cost of $25. The cost estimate (e.g., based on the number of processors and the proprietary data) is shown in field 408 and the runtime estimate is shown in field 410. In some embodiments, a cost estimate also takes into consideration other allocated resources, such as allocated ports (e.g., some processing runs may be I/O intensive whereas other are not) and/or allocated storage.

If the proposed processing run is acceptable, the user presses submit button 414. Depending upon the approval settings specified via radio buttons 216 in FIG. 2, the processing run is either initiated or is sent to the contact (e.g., specified in fields 218 and 220 in FIG. 2) for approval. If the user wants to modify the proposed processing run (e.g., to reduce cost or to modify the type of process to perform), go back button 412 is pressed.

Figure 5:
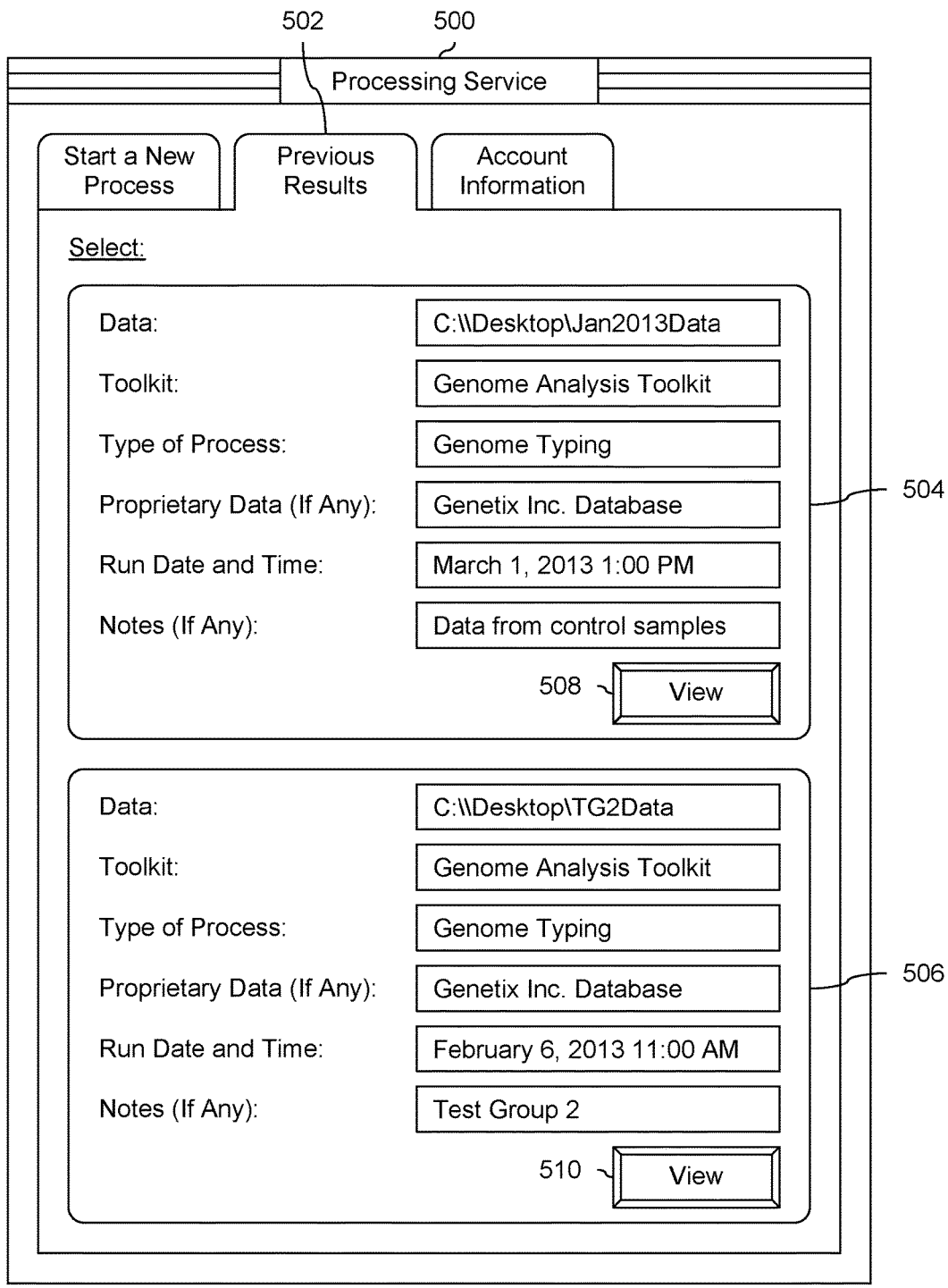
FIG. 5 is a diagram showing an embodiment of a user interface in which a previous processing run is viewed.

FIG. 5 is a diagram showing an embodiment of a user interface in which a previous processing run is viewed. In the example shown, tab 502 (i.e., previous results) is selected in user interface 500. In some embodiments, all previous processing runs are saved automatically. In some embodiments, only selected processing runs are saved. In some embodiments, there is a cost associated with saving processing results and a quote is presented (e.g., similar to FIG. 4) before a processing run is saved (not shown).

In tab 502, two previous processing runs are shown in frames 504 and 506. For each processing run presented, the data (e.g., C:\\Desktop\Jan2013Data or C:\\Desktop\Jan2013Data), the toolkit, type of process, proprietary data (if any), run date and time, and notes (if any) are displayed. To view a selected processing run, the corresponding view button (e.g., button 508 or 510) is selected.

FIG. 6 is a diagram showing an embodiment of a user interface which shows account information. In the example shown, tab 602 (i.e., account information) is selected in user interface 600. Account activity section 610 shows credits, debits, and remaining budget for various transactions associated with the account. Tab 602 continues the example of FIG. 2 where a user specified a budget of $10,000 in field 212. The remaining budget column in account activity section 610 begins with a budget of $10,000 and deducts the costs of processing runs from that $10,000 budget. For example, at 612 the Feb. 6, 2013 processing run cost $205 and the remaining budget is updated to $10,000−$205=$9,795. At 614, the Feb. 15, 2013 payment of $205 does not cause the remaining budget to change (at least in this example). The remaining budget is updated again at 616 for the Mar. 1, 2013 processing run: $9,795−$190=$9,605.

Account settings are shown in section 620 and at least some of the information shown in that section is set via user interface 200 in FIG. 2. For example, the school, department/institute, and lab/principal investigator displayed in fields 622, 624, and 626, respectively are set via user interface 200 in FIG. 2. The budget information (displayed in field 628 and radio buttons 630) and permission information (displayed in radio buttons 632 and fields 634 and 636) are also specified via user interface 200 in FIG. 2. If desired, account settings shown in section 620 may be changed using the user interface shown.

Figure 7:
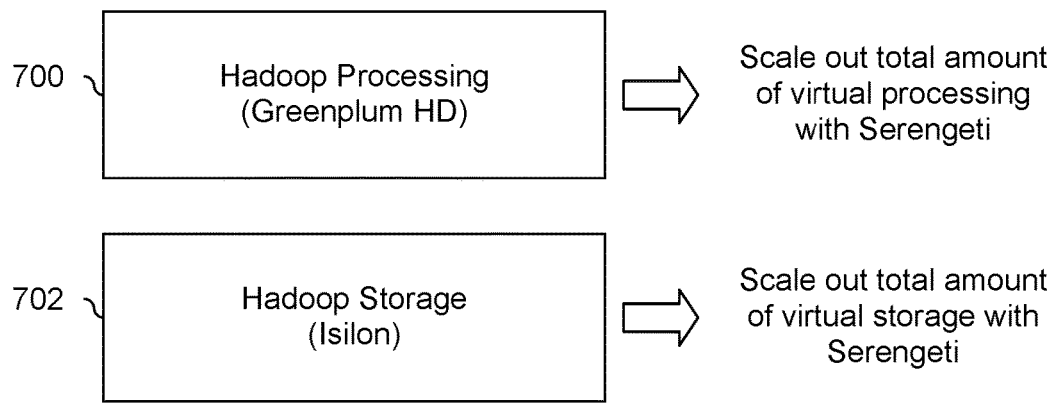
FIG. 7 is a diagram showing an embodiment of a decoupled processing and storage associated with a Hadoop system.

FIG. 7 is a diagram showing an embodiment of a decoupled processing and storage associated with a Hadoop system. This example shows one embodiment of a system which has a total amount of storage which is independent of a total amount of processing associated. In this example, Hadoop processing 700 is implemented using Greenplum HD and Hadoop storage 702 is implemented using Isilon.

In this example, Hadoop processing 700 and Hadoop storage 702 are virtualized and so a virtual infrastructure manager, such as Serengeti, has the ability to separately scale out the total amount of virtual processing or the total amount of virtual storage. For example, if users are increasing their utilization of a processing system (e.g., because more new users are signing up or because each user is submitting more processing requests) but the total amount of storage is sufficient, Hadoop processing 700 can be scaled out using Serengeti without being forced to scale out Hadoop storage 702. Similarly, if more storage is desired but the total amount of processing resources is sufficient, Hadoop storage 702 may be scaled out without having to scale out Hadoop processing 700 unnecessarily.

One advantage to using Isilon (or some other alternative with similar capabilities) is that Hadoop storage 702 can be scaled out to very large sizes. For applications with very large datasets (e.g., genome data), a single file system in Hadoop storage 702 can be scaled out to 16 petabytes.

Another advantage to using Isilon (or some similar alternative) is that Isilon supports multiple protocols, such as network file system (NFS), common Internet file system (CIFS), and Hadoop Distributed File System (HDFS) on a single storage platform. This reduces extract, transfer, and load (ETL) experienced by the system. In contrast, some other systems which do not use Isilon (or some similar alternative) have to extract, transfer, and load the data onto another storage platform if a desired protocol is not supported.

Figure 8A:
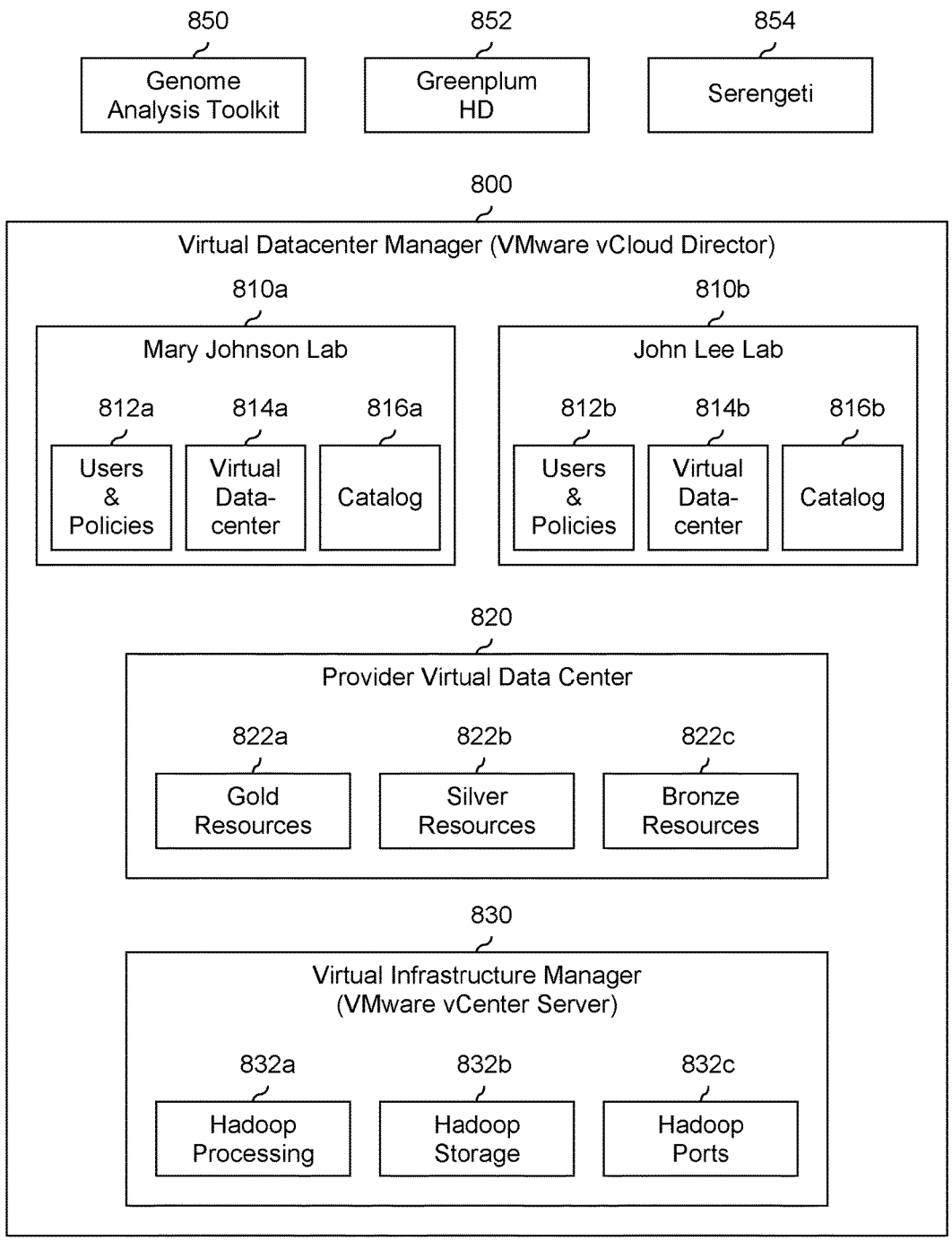
FIG. 8A is a diagram showing an embodiment of a processing system which provides processing services to one or more users.

FIG. 8A is a diagram showing an embodiment of a processing system which provides processing services to one or more users. In the example shown, FIG. 8A is one embodiment of a system which performs the process shown in FIG. 1B. Virtual datacenter manager 800 provisions and manages virtual datacenters and in one example is implemented using VMware vCloud Director. Virtual datacenter manager 800 enables multiple users (such as the researchers Mary Johnson and John Lee) to be serviced by the same system while keeping information associated with each user secure. For example, instance 810a is associated with the Mary Johnson lab or account and instance 810b is associated with the John Lee lab or account.

Each of instances 810a and 810b includes users and policies (812a and 812b), a virtual data center (814a and 814b), and a catalog (816a and 816b). Users and policies 812a and 812b include (at least) user and policy information associated with the Mary Johnson lab and John Lee lab, respectively. For example, it may have policies about whether permission is required to perform a processing run, the amount of a remaining budget, etc. In some embodiments, users and policies 812a and 812b are identical and include information for all users.

Virtual data centers 814a and 814b are secure and unique data centers for the dedicated use of the associated user (i.e., Mary Johnson and John Lee, respectively). A user associated with instance 810a cannot (for example) access the results of processing run on virtual datacenter 814b and vice versa. Any of a variety of tools or applications may be run on virtual datacenter 814a or 814b. For example, genome analysis toolkit 850, Greenplum HD 852, and/or Serengeti 854 may be run on virtual datacenter 814a or 814b as desired.

Catalogs 816a and 816b are catalogs of services that are available to the users or instances.

Virtual datacenters 814a and 814b are implemented using either gold resources 822a, silver resources 822b, bronze resources 822c or a combination of resources types from the provider virtual data center 820. Provider virtual data center 820 assembles groups of resources 822a-822c and allocates groups of resources for virtual datacenter 814a or 814b as appropriate for that particular user. For example, the quantity and/or quality of resources in gold resources 822a is better than silver resources 822b, which in turn is better than bronze resources 822c. For example, gold resources 822a may have more processing resources and/or storage resources than silver resources 822b. Accordingly, costs (in embodiments where costs are charged to the user) vary accordingly. In other words, gold resources 822a cost more than silver resources 822b and silver resources 822b costs more than bronze resources 822c. To meet the cost constraint of a given user (e.g., the Mary Johnson Lab may have a bigger budget to work with than the John Lee Lab), a group of resources is allocated based (at least in some embodiments) on a cost cap. Provider virtual data center 820 provides resource abstraction services and vCloud Director performs resource allocation steps outlined in 102 and 106 in FIG. 1B.

Each of the groups of resources 822a-822c includes some Hadoop processing resources (832a), Hadoop storage resources (832b), and Hadoop port resources (832c) from virtual infrastructure manager 830. In this example, virtual infrastructure manager 830 is implemented using VMware vCenter Server. If desired, the total amount of Hadoop processing 832a, Hadoop storage 832b, and/or Hadoop ports 832c may be scaled out (e.g., independently) using (for example) Serengeti.

In some embodiments, processing system 800 is built on or using converged infrastructure, such as Vblock. Converged Infrastructure provides best of breed Compute (Cisco UCS), Storage (EMC VNX and VMAX), Network infrastructure (Cisco Nexus) and virtualization software (VMware vCloud Suite) in a factory built, pre-validate and fully integrated infrastructure stack. In today's cloud environments where scaling up and/or out the underlying resources quickly is key to success, vBlock allows service providers in this space such as university or research facilities to quickly add resource to their service offering. vBlock customers benefit from optimized performance, joint product roadmap across all components, upgrade paths across the entire infrastructure stack and a single support organization.

Figure 8B:
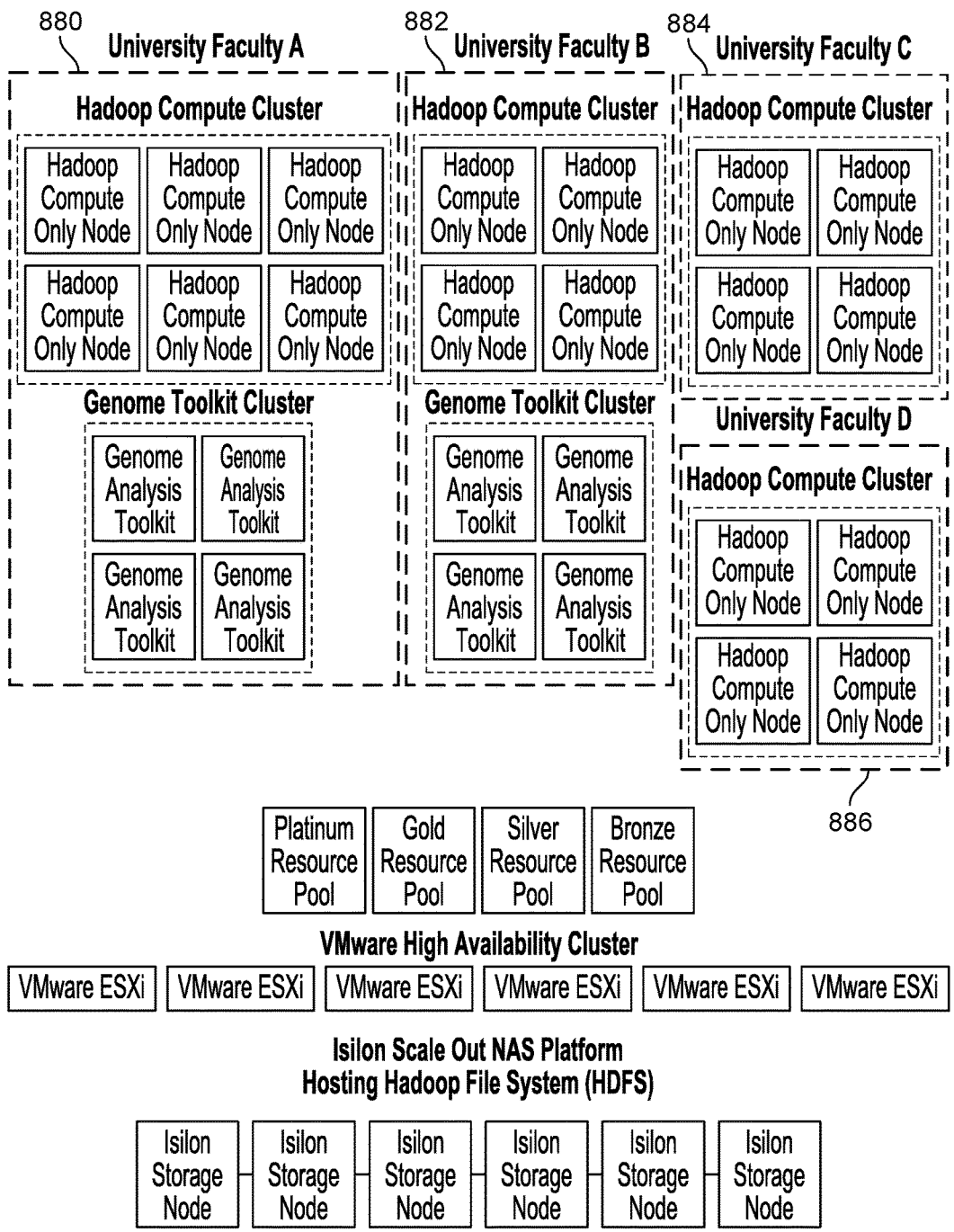
FIG. 8B is a diagram showing a second embodiment of a processing system which provides processing services to one or more users.

FIG. 8B is a diagram showing a second embodiment of a processing system which provides processing services to one or more users. In the example shown, there are four systems associated with four different university faculty members. Each faculty member has a system which includes a Hadoop compute cluster with various numbers of Hadoop compute only nodes: university faculty member A (880) has 6 Hadoop compute only nodes, university faculty member B (882) has 4 Hadoop compute only nodes, university faculty member C (884) has 4 Hadoop compute only nodes, and university faculty member D (886) has 4 Hadoop compute only nodes. Some faculty members also have systems which include a genome toolkit cluster while others do not. For example, university faculty members A and B (880 and 882) each have a genome tool kit cluster (with 4 genome analysis toolkits each), whereas university faculty members C and D (884 and 886) do not have a genome toolkit cluster.

A benefit to the embodiments of the processing system described herein is that selected information may be shared with collaborators without exposing confidential information outside of the scope of the collaboration. For example, within a given lab there are typically multiple research projects being worked on at the same time. One set of graduate students and/or postdoctoral candidates may be working on one research project while another set is working on another project. If the first group is collaborating with another lab, that group will want to share project information with the other lab. However, it would not be desirable to share research that the second set of graduate students and/or postdoctoral candidates is working on. The following figures show some example user interfaces in which sharing is enabled, but without the risk of exposing confidential information.

Figure 9:
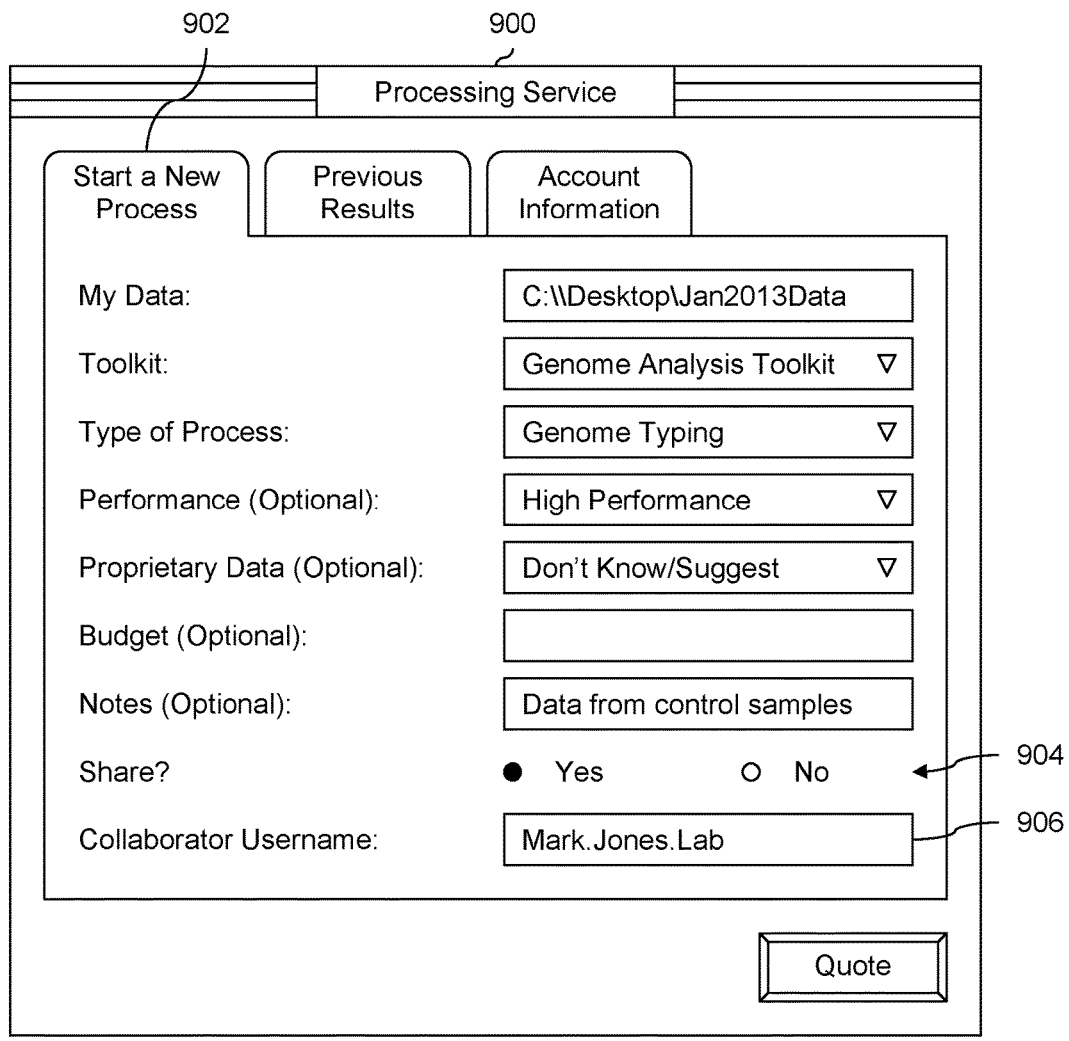
FIG. 9 is a diagram showing an embodiment of a user interface in which sharing is enabled when a new processing run is specified.

FIG. 9 is a diagram showing an embodiment of a user interface in which sharing is enabled when a new processing run is specified. In the example shown, tab 902 in user interface 900 is similar to tab 302 in user interface 300 in FIG. 3, except tab 902 has some additional user interface controls. In tab 902, a user specifies via radio buttons 904 whether the processing run is to be shared. If so, the collaborator username (e.g., Mark.Jones.Lab) is obtained via fillable field 906.

In this particular example, the collaborator username specified in fillable field 906 is associated with the processing system which provides user interface 900, making it a quick and unique way of identifying a collaborator. In some embodiments, additional information associated with a collaborator is determined based on the username specified in fillable field 906 and is displayed (e.g., in real time) in tab 902 (not shown). For example, there may be two researchers named Mark Jones and displaying other information (e.g., company, university, school, department, e-mail address, etc.) associated with the specified collaborator username may be useful to ensure that the proper collaborator is selected by the user.

Figure 10:
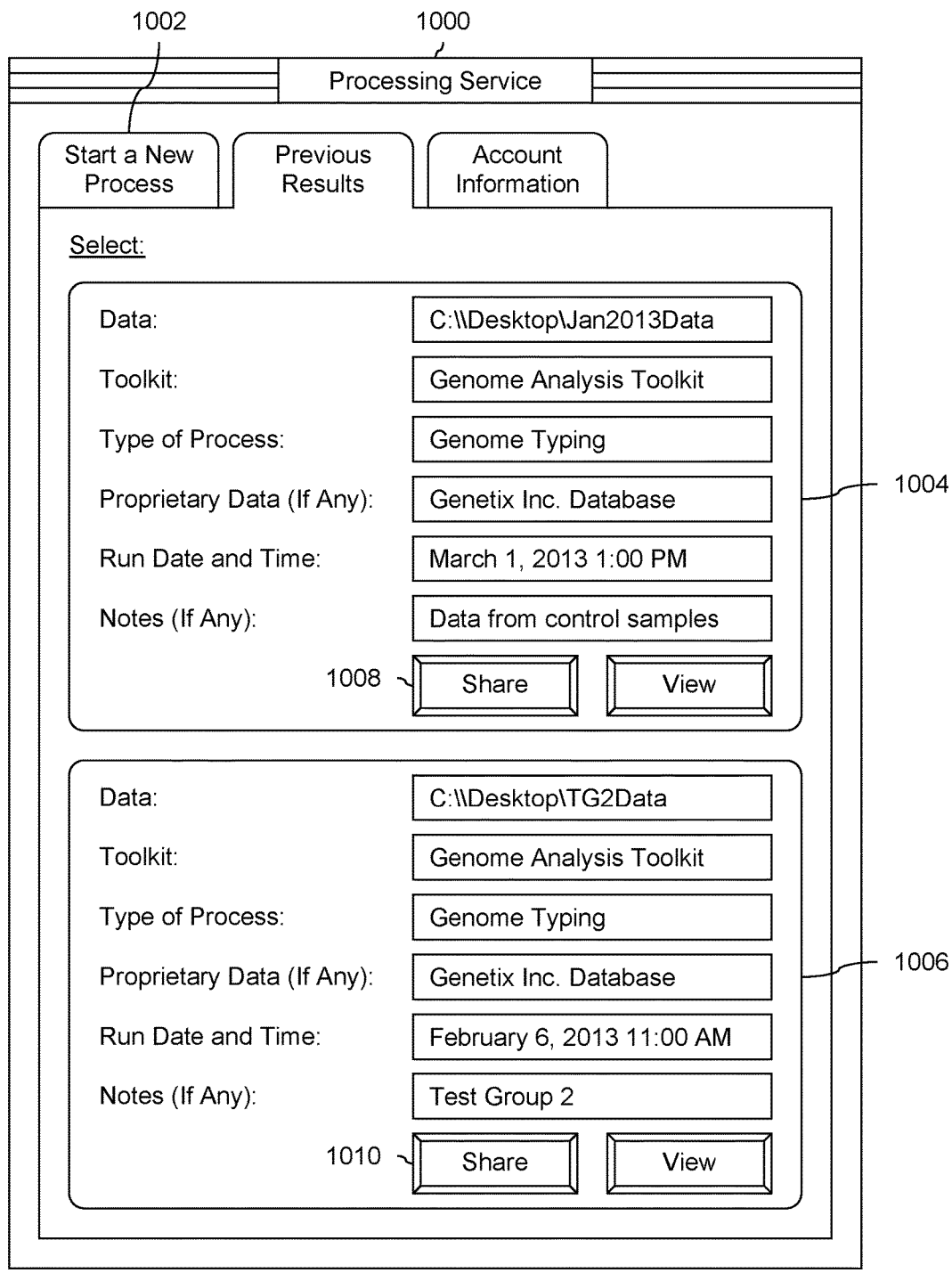
FIG. 10 is a diagram showing an embodiment of a user interface in which sharing is enabled after processing has been performed.

FIG. 10 is a diagram showing an embodiment of a user interface in which sharing is enabled after processing has been performed. In the example shown, tab 1002 in user interface 1000 is similar to tab 502 in user interface 500 in FIG. 5, except tab 1002 has some additional user interface controls. If a user wants to share data from processing run 1004 with a collaborator, share button 1008 is pressed which causes a window to be displayed in which the collaborator is identified (not shown). Similarly, if a user wants to share data from processing run 1006, share button 1010 is pressed. Any number of processing runs may be shared with any number of collaborators and a collaborator may be specified in any number of ways.

The user interfaces shown in FIGS. 9 and 10 are not necessarily mutually exclusive. In some embodiments, even if a user does not enable sharing when a processing run is being specified (e.g., as in FIG. 9), the user still has the option of sharing data from that processing run after processing has completed (e.g., as in FIG. 10).

In the backend, sharing may be performed using any appropriate application or tool. In one example, Greenplum Chorus is used to share data between collaborators by offering users the ability share selected data with specified collaborators. This enables a lab or principal investigator to share data related to a collaboration with a collaborator, without exposing data unrelated to the collaboration which would be undesirable because of the risk of being "scooped." A lab or principal investigator may be working on multiple projects simultaneously, and a collaborator on one project may be a competitor on another project. Referring back to FIGS. 7 and 8 using Greenplum Chorus with the exemplary systems shown therein may be attractive because Greenplum Chorus is designed to operate seamlessly with the system components shown. For other systems, there may be some other sharing application or tool which works better with those embodiments.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:
a hardware processor; and
a memory coupled with the hardware processor, wherein the memory is configured to provide the hardware processor with instructions which when executed cause the processor to:
 decide whether to increase a total amount of storage in a pool of Hadoop storage;
 decide whether to increase a total amount of processing in a pool of Hadoop processing;
 in the event it is decided to: (1) increase the total amount of storage in the pool of Hadoop storage and (2) not increase the total amount of processing in the pool of Hadoop processing, increase the total amount of storage in the pool of Hadoop storage without increasing the total amount of processing in the pool of Hadoop processing; and
 in the event it is decided to: (1) not increase the total amount of storage in the pool of Hadoop storage and (2) increase the total amount of processing in the pool of Hadoop processing, increase the total amount of processing in the pool of Hadoop processing without increasing the total amount of storage in the pool of Hadoop storage, wherein in response to receiving a request to perform a process on a set of data:
  one or more storage resources from the pool of Hadoop storage is allocated, including a Hadoop file system; and
  one or more processing resources from the pool of Hadoop processing is allocated, including a virtual and customized Hadoop compute node wherein an application or toolkit which runs on the virtual and customized Hadoop compute node is decoupled from a specific implementation of an underlying processor below a virtualization, including by:
   storing a Hadoop compute node as a template;
   deploying the Hadoop compute node stored as the template in order to obtain a default virtual Hadoop compute node; and
   customizing the default virtual Hadoop compute node in order to obtain the virtual and customized Hadoop compute node, including by using a custom script to link the virtual and customized Hadoop compute node to the Hadoop file system.

2. The system recited in claim 1, wherein the pool of Hadoop processing includes one or more of the following: virtual processing or Greenplum HD.

3. The system recited in claim 1, wherein the pool of Hadoop storage includes one or more of the following: virtual storage, Isilon, a storage technology that supports a plurality of file system protocols on a single storage platform, or a storage technology that supports petabytes of storage.

4. The system recited in claim 1, wherein the set of data includes genome data and a genome analysis toolkit runs on the allocated processing and the allocated storage.

5. A method, comprising:
using a processor to decide whether to increase a total amount of storage in a pool of Hadoop storage;
using the processor to decide whether to increase a total amount of processing in a pool of Hadoop processing;
in the event it is decided to: (1) increase the total amount of storage in the pool of Hadoop storage and (2) not increase the total amount of processing in the pool of Hadoop processing, using the processor to increase the total amount of storage in the pool of Hadoop storage without increasing the total amount of processing in the pool of Hadoop processing; and
in the event it is decided to: (1) not increase the total amount of storage in the pool of Hadoop storage and (2) increase the total amount of processing in the pool of Hadoop processing, using the processor to increase the total amount of processing in the pool of Hadoop processing without increasing the total amount of storage in the pool of Hadoop storage, wherein in response to receiving a request to perform a process on a set of data:
 one or more storage resources from the pool of Hadoop storage is allocated, including a Hadoop file system; and
 one or more processing resources from the pool of Hadoop processing is allocated, including a virtual and customized Hadoop compute node wherein an application or toolkit which runs on the virtual and customized Hadoop compute node is decoupled from a specific implementation of an underlying processor below a virtualization, including by:
  storing a Hadoop compute node as a template;

deploying the Hadoop compute node stored as the template in order to obtain a default virtual Hadoop compute node; and customizing the default virtual Hadoop compute node in order to obtain the virtual and customized Hadoop compute node, including by using a custom script to link the virtual and customized Hadoop compute node to the Hadoop file system.

6. The method recited in claim 5, wherein the pool of Hadoop processing includes one or more of the following: virtual processing or Greenplum HD.

7. The method recited in claim 5, wherein the pool of Hadoop storage includes one or more of the following: virtual storage, Isilon, a storage technology that supports a plurality of file system protocols on a single storage platform, or a storage technology that supports petabytes of storage.

8. The method recited in claim 5, wherein the set of data includes genome data and a genome analysis toolkit runs on the allocated processing and the allocated storage.

9. A computer program product, the computer program product being embodied in a non-transitory computer readable storage medium and comprising computer instructions for:

deciding whether to increase a total amount of storage in a pool of Hadoop storage;

deciding whether to increase a total amount of processing in a pool of Hadoop processing;

in the event it is decided to: (1) increase the total amount of storage in the pool of Hadoop storage and (2) not increase the total amount of processing in the pool of Hadoop processing, increasing the total amount of storage in the pool of Hadoop storage without increasing the total amount of processing in the pool of Hadoop processing; and in the event it is decided to: (1) not increase the total amount of storage in the pool of Hadoop storage and (2) increase the total amount of processing in the pool of Hadoop processing, increasing the total amount of processing in the pool of Hadoop processing without increasing the total amount of storage in the pool of Hadoop storage, wherein in response to receiving a request to perform a process on a set of data:

one or more storage resources from the pool of Hadoop storage is allocated, including a Hadoop file system; and one or more processing resources from the pool of Hadoop processing is allocated, including a virtual and customized Hadoop compute node wherein an application or toolkit which runs on the virtual and customized Hadoop compute node is decoupled from a specific implementation of an underlying processor below a virtualization, including by:

storing a Hadoop compute node as a template;

deploying the Hadoop compute node stored as the template in order to obtain a default virtual Hadoop compute node; and customizing the default virtual Hadoop compute node in order to obtain the virtual and customized Hadoop compute node, including by using a custom script to link the virtual and customized Hadoop compute node to the Hadoop file system.

10. The computer program product recited in claim 9, wherein the pool of Hadoop processing includes one or more of the following: virtual processing or Greenplum HD.

11. The computer program product recited in claim 9, wherein the pool of Hadoop storage includes one or more of the following: virtual storage, Isilon, a storage technology that supports a plurality of file system protocols on a single storage platform, or a storage technology that supports petabytes of storage.

12. The computer program product recited in claim 9, wherein the set of data includes genome data and a genome analysis toolkit runs on the allocated processing and the allocated storage.

13. The system recited in claim 1, wherein the data center provider is further configured to: in response to receiving the request to perform the process on the set of data, allocate one or more ports from a pool of Hadoop ports, wherein the total number of ports in the pool of Hadoop ports is able to be scaled out independently of the total amount of processing in the pool of Hadoop processing and the total amount of storage in the pool of Hadoop storage.

14. The method recited in claim 5, further comprising: in response to receiving the request to perform the process on the set of data, allocating one or more ports from a pool of Hadoop ports, wherein the total number of ports in the pool of Hadoop ports is able to be scaled out independently of the total amount of processing in the pool of Hadoop processing and the total amount of storage in the pool of Hadoop storage.

15. The computer program product recited in claim 9, further comprising computer program instructions for: in response to receiving the request to perform the process on the set of data, allocating one or more ports from a pool of Hadoop ports, wherein the total number of ports in the pool of Hadoop ports is able to be scaled out independently of the total amount of processing in the pool of Hadoop processing and the total amount of storage in the pool of Hadoop storage.

16. The system recited in claim 1, wherein:

the Hadoop file system is stored on a scale out network-attached storage platform; and the scale out network-attached storage platform supports a plurality of protocols on a single storage platform, including one or more of the following protocols: network file system (NFS), common Internet file system (CIFS), or Hadoop Distributed File System (HDFS).

17. The method recited in claim 5, wherein:

the Hadoop file system is stored on a scale out network-attached storage platform; and the scale out network-attached storage platform supports a plurality of protocols on a single storage platform, including one or more of the following protocols: network file system (NFS), common Internet file system (CIFS), or Hadoop Distributed File System (HDFS).

18. The computer program product recited in claim 9, wherein:

the Hadoop file system is stored on a scale out network-attached storage platform; and the scale out network-attached storage platform supports a plurality of protocols on a single storage platform, including one or more of the following protocols: network file system (NFS), common Internet file system (CIFS), or Hadoop Distributed File System (HDFS).

* * * * *